(12) United States Patent
Field et al.

(10) Patent No.: US 9,987,203 B1
(45) Date of Patent: Jun. 5, 2018

(54) METHODS OF REDUCING RED WINE STAINS ON TEETH

(71) Applicant: Unwined, Inc., Bunnell, FL (US)

(72) Inventors: Jeffrey A. Field, Bunnell, FL (US); Dennis L. Lott, Bunnell, FL (US)

(73) Assignee: Unwined, Inc, Bunnell, FL (US)

( * ) Notice: Subject to any disclaimer, the term of this patent is extended or adjusted under 35 U.S.C. 154(b) by 0 days. days.

(21) Appl. No.: 15/185,161

(22) Filed: Jun. 17, 2016

Related U.S. Application Data (60) Provisional application No. 62/180,912, filed on Jun. 17, 2015.

(51) Int. Cl.
| | | |
|---|---|---|
| *A61Q 11/00* | (2006.01) | |
| *A61K 8/19* | (2006.01) | |
| *A61K 8/24* | (2006.01) | |
| *A61K 8/25* | (2006.01) | |
| *A61K 8/84* | (2006.01) | |
| *A61Q 11/02* | (2006.01) | |

(52) U.S. Cl.
CPC ............... *A61K 8/19* (2013.01); *A61K 8/24* (2013.01); *A61K 8/25* (2013.01); *A61K 8/84* (2013.01); *A61Q 11/02* (2013.01)

(58) Field of Classification Search
None
See application file for complete search history.

(56) References Cited

U.S. PATENT DOCUMENTS

| | | | | |
|---|---|---|---|---|
| 2004/0101493 A1* | 5/2004 | Scott | ........................ | A61K 8/19 424/49 |
| 2007/0196474 A1* | 8/2007 | Withiam | ................... | A61K 8/19 424/465 |
| 2008/0102041 A1* | 5/2008 | Alden | ...................... | A61K 8/02 424/49 |
| 2014/0227202 A1* | 8/2014 | Pilgaonkar | ........... | A61K 8/0216 424/52 |

* cited by examiner

*Primary Examiner* — Brian Gulledge
(74) *Attorney, Agent, or Firm* — Christopher & Weisberg, P.A.

(57) ABSTRACT

A method of improving the cosmetic appearance of human teeth comprising the step of contacting the teeth with a whitening powder composition after ingesting a chromogenic, tannin-containing food or beverage and thereby reducing staining of the teeth caused by tannins and/or chromogens. The tooth-whitening tablet is comprised of (i) at least one abrasive powder; (ii) at least one buffering powder; (iii) a complexing agent; and, optionally, (iv) an anti-cavity sweetener.

20 Claims, 8 Drawing Sheets

Fig. 9

METHODS OF REDUCING RED WINE STAINS ON TEETH

FIELD OF INVENTION

Methods and compositions for improving the cosmetic appearance of human teeth, especially reducing stains from red wine and other tannin-containing foods and beverages (such as but not limited to tobacco, food coloring, coffee, tea, white wine, berries, beer), as well as other chromogenic materials introduced into the oral cavity that can ultimately lead to tooth staining

BACKGROUND OF THE INVENTION

The health benefits of red wine are widely reported in the medical/scientific literature. Red wine is thought to prevent damage to blood vessels, reduces low-density lipoprotein (LDL) cholesterol (the "bad" cholesterol) and prevent blood clots. Additionally, phenolic extracts in wine have been reported to reduce the growth of bacteria in the oral cavity. http://www.allure.com/beauty-trends/blogs/daily-beauty-reporter/2014/12/red-wine-prevent-cavities.html However, consumption of red wine is also known to have undesirable or negative consequences from an oral health perspective. The acid pH of red wine demineralizes teeth causing enamel to become softened, thinned and eroded. The thinner enamel layer, in turn, makes underlying dentin more visible, creating the appearance of yellow and brown teeth. With less enamel, teeth have increased porosity, allowing light absorbing species, chromogens to enter and bind to the tooth. Additionally, tannins in red wine stain teeth.

Dentrifices are the most widely known dosage forms used to whiten or lighten the appearance of teeth. Representative of the whitening dentrifices is Level Wintermint Five Whitening Formula Anticavity Toothpaste sold by Level Oral Care LLC (Jacksonville, Fla.), which contains three abrasive agents—calcium carbonate, sodium bicarbonate and hydrated silica—as well as other excipients (xylitol, sorbitol, glycerin, carboxymethyl-cellulose sodium, sodium lauryl sulfate, sodium pyrophosphate, sodium benzoate, and saccharin sodium.) However, brushing teeth after drinking red wine—with the intention of removing staining tannins and residual sugar (a potential source of food for cariogenic bacteria)—can have unintended deleterious consequences. Mechanical abrasion (i.e., from the bristles of the toothbrush and the abrasives in toothpaste) scrapes protective minerals off the surface of teeth which, as discussed above, are softer from exposure to the acidic environment created by the wine. Over time, this damage will cause the staining from tannins and chromogens to be increased, not reduced.

Teeth whitening gums may contain small amounts of abrasives. Nicorette® Fresh Mint Gum, sold by GlaxoSmithKline Consumer Healthcare LP, is representative of gums marketed as having teeth whitening properties; it contains sodium bicarbonate as an abrasive agent as well as other excipients, including waxes (acacia, carnauba), gum base, pH adjusters, magnesium oxide, menthol, peppermint oil, sodium carbonate, titanium dioxide, and xylitol. However, the principle mechanism of action of gums is dilution—neutralizing the acidity in the oral cavity by increasing salivary flow through mastication. Teeth whitening gums have several inherent limitations. Active, sustained chewing and secretion of the salivary glands is required. Additionally, whitening gums are not effective in certain subsets of the population having xerostomia or hyposalivation.

Another popular cosmetic method for reducing teeth stains caused by red wine and other staining chromogens is bleaching—typically with peroxides (hydrogen peroxide or carbamide peroxide). However, like mechanical abrasion, peroxide bleaching can increase staining—not only by increasing enamel porosity but also by creating rougher (i.e., less smooth) teeth surfaces. (Rougher teeth create more surface area for chromogen binding and tannin staining.) Peroxide bleaching can have other negative sequelae—short-term irritation of the teeth and surrounding gums and long-term hypersensitivity.

Wipes—fabrics impregnated with buffering solutions containing abrasives—have also been marketed to remove wine and other stains. This product class is limited in several respects. The buffering action of wipes is limited to teeth whose surfaces are contacted; the pH of the saliva and oral mucosae remains acidic and largely negates localized buffering. The negative effect of this acid environment on teeth is exacerbated by demineralization (i.e., from scraping action of abrasive impregnated into the wipe).

Tooth brushing, peroxide bleaching, gum chewing and wipes, all suffer from usability limitations—particularly in connection with the wine consuming experience (i.e., where wine is sipped, tasted, and savored in a social setting. Tooth brushing and peroxide bleaching require active effort on the part of the consumer—use a specific implements/appliance in a private environment for a prescribed period of time. Likewise, as discussed above, whitening gums require sustained chewing. Moreover, when consuming wine (e.g., at a meal or social function) gum is not chewed; doing so would detract from the taste and overall pleasure of the wine drinking. Applying wipes requires introducing germ-covered fingers into the oral cavity and can be socially awkward. Moreover, wipes are not pleasant from a sensory perspective—taste and texture.

Accordingly, there has been, and remains, a need for a cosmetic teeth-whitening treatment that can (a) be accomplished quickly and inconspicuously in a social environment by a user that (b) reduces the appearance of teeth stains from, but not limited to tannin-containing foods, beverages, or other chromogens introduced into the oral cavity, in particular red wine, and (c) that avoids (i) weakening the enamel, (ii) increasing porosity, (iii) irritating the teeth or gums, and/or (iv) causing hypersensitivity. Those needs are met by methods and compositions of the present invention. In short, the methods of using the inventive compositions of the present invention (both in tablet and free-flowing powder form) provide a means for enjoyably consuming red wine while reducing staining from tannins and other staining chromogenic materials introduced to the oral cavity. The present invention is also a proactive measure to maintain a bright white and healthy smile while on the go, utilizing a multi-tiered system for stain removal and prevention.

SUMMARY OF THE INVENTION

A method of safely improving the cosmetic appearance of human teeth comprising the step of contacting the teeth with a tooth-whitening powder composition (preferably, a tablet) after introducing a chromogenic material into the oral cavity and thereby reducing staining of the teeth caused by tannins (especially from wines, most especially red wines) and chromogens, wherein the tooth-whitening tablet includes, as essential elements, (i) at least one, preferably at least two, abrasive powders; (ii) at least one, preferably at least two, buffering powders; (iii) a complexing agent, and optionally, but preferably, (iv) an anti-cavity sweetener. Optionally, but preferably, the tooth-whitening powder composition used to practice the methods of the present invention contains a calcium phosphate compound to promote remineralization.

In preferred embodiments, the method of the present invention consists essentially, and in even more preferred embodiments consists of, passively contacting the teeth with the above-described tooth-whitening powder. For purposes of the present invention, brushing, using wipes, or bleaching are not passively contacting.

In embodiments of the invention where the tooth-whitening powder composition is in the form of a tablet, by "passively contacting" is meant crushing, breaking, or allowing to dissolve the tablet by limited mastication, but not sustained chewing as is the case when using a gum.

In tablet and powder embodiments, passively contacting can include swooshing and/or spreading the broken down tablet in the oral cavity with the tongue, but does not include use of a manual personal care implement (i.e., a tooth brush or a wipe).

The methods of the present invention are practiced in a "social setting"—venues, public or private, in which more than one person interact and consume food and/or beverages. Non-limiting examples of social settings include bars, restaurants, cafes as well as dinner parties, receptions.

As used in the present application, the terms in quotations are to be understood in the context of the methods of the present invention as having the following definitions:

"Improving the cosmetic appearance of human teeth" means making teeth appear whiter (by which is meant, as non-limiting examples, less yellow, red, blue, or brown) and/or lighter (i.e., less dark).

"Tannins" are polyphenolic compounds that bind to and precipitate proteins.

"Safely" reduces stains refers to the use of abrasives to remove stains while the oral cavity is concomitantly buffered to a less acidic pH, resulting in re-hardening the tooth and enamel making it less prone to abrasive damage.

"Red wine" is a tannin-containing, chromogenic food having a red, purple or brown color derived from in part from the skins of dark-colored grapes. Red wine grapes are fermented with seeds, skins and often pieces of stems, producing condensed tannins. Finished wine pH, after fermentation, can be between 3.3 and 3.8, depending on the tannin content. Non-limiting examples of varieties of red wines that are staining tanin-containing foods within the scope of the present invention include the following: Barbera; Cabernet Franc; Cabernet Sauvignon; Carmenère; Catawba; Chambourcin; Charbono; Concord; Grenache; Lagrein; Malbec; Merlot; Montepulciano; Muscadine; Nebbiolo; Norton; Petit Verdot; Petite Sirah; Pinotage; Pinot Noir; Primitivo; Sagrantino; Sangiovese; Syrah; Tempranillo; and Zinfandel.

"Chromogen" or "chromogenic compound" is a substance that stains the teeth when introduced into the oral cavity. Individual compounds per se may be chromogenic or may react with or otherwise combine in the oral cavity to form chromogenic compounds. Non-limiting examples of chromogenic compounds include red wine, white wine, tea, coffee, berries, food coloring, tobacco, and beer.

"Ingesting" means introducing the tablet into the oral cavity and allowing the tablet to remain in the oral cavity for a sufficient period of time to have the desired anti-staining effect. This could include mild agitation in the oral cavity (e.g., by swooshing).

A "complexing agent" is an ingredient that binds to and facilitates the removal of chromogenic compounds.

In preferred embodiments, the teeth whitening powder compositions used in the methods of the present invention contains two carbonate compounds selected from the group consisting of sodium bicarbonate and calcium carbonate, which can serve as both an abrasive powder and/or a buffering powder.

Sodium bicarbonate is an inorganic salt that conforms to the formula $NaHCO_3$ that neutralizes acids in oral cavity. The $14^{th}$ Edition of the International Cosmetic Ingredient Dictionary and Handbook (INCI Dictionary) published by the Personal Care Products Council also classifies sodium bicarbonate as an oral care agent with abrasive properties used to polish teeth, deodorize the breath, and provide other cosmetic benefits. In tablet dosage forms used in practicing the methods of the present invention, sodium bicarbonate is ingested in an amount of at least 1 mg, more preferably 3-15 mg.

Calcium Carbonate is an inorganic salt that conforms to the formula $CaCO_3$. Like sodium bicarbonate it is a multi-functional ingredient used in oral care products for abrasive tooth cleaning; it is also used as a buffering, opacifying and/or bulking agent. In tablet dosage forms used in practicing the methods of the present invention, calcium carbonate comprises at least 10 mg, preferably 50 mg, and most preferably 87.5 to 125 mg.

In preferred embodiments, the teeth-whitening powder compositions used to practice the methods of the present invention includes a calcium phosphate compound that acts as an abrasive powder and/or a re-mineralization agent. A preferred calcium phosphate compound is dicalcium phosphate (empirical formula—$Ca.HPO_4$). In certain methods of the present invention, dicalcium phosphate is administered (i.e., ingested) in an amount of at least 10 mg, preferably 20 mg, and even more preferably 30-60 mg.

Silica compounds are inorganic oxides that conform generally to the formula $SiO_2$, and are suitable as abrasive powders in teeth-whitening powder compositions used in practicing methods of the present invention. For purposes of the present invention, silica can be untreated, hydrated or fumed. It is classified in the INCI Dictionary as an abrasive, an ingredient that removes unwanted materials from various body surfaces, including tannin-containing foods. In methods of the present invention, silica is administered (ingested) in an amount of at least 0.5 mg, preferably at least 1.0 mg and still more preferably at least 2 mg.

In certain embodiments of the present invention, the at least one (preferably at least two) abrasive powder(s) and the at least one (preferably at least two) buffering powders are combined with a complexing agent, and, optionally but preferably, an anti-cavity sweetener.

A particularly preferred complexing agent suitable for use in the methods and compositions of the present invention is polyvinylpyrrolidone ("PVP"). PVP is a linear polymer formed from 1-vinyl-2-pyrrolidone monomers conforming generally to the formula:

In practicing the methods of the present invention, PVP is used as a complexing agent and is ingested in an amount of at least 10 mg, preferably 25 mg, and still more preferably 50-100 mg.

In practicing the methods of the present invention, a non-cariogenic sweetner, preferably, but not limited to, the pentahydric alcohol xylitol ($C_5H_{12}O_5$) is utilized.

One or more of chemical excipients known in the art may be incorporated in the tablet, powder or other similar dosage forms used practicing the methods of the present invention. A non-limiting list of these excipients includes: pH adjusters; preservatives; diluents, glidants/lubricants; moisture scavengers binders, compression aids, disintegrants (to promote tablet break-up); sweeteners or flavoring agents; and/or pigments or colorants. Additionally, dosage forms used in practicing the methods of the present invention may include one or more bio-functional ingredients, including, antioxidants, vitamins, minerals, fluoride sources, amino acids, and/or probiotics.

In certain embodiments, the above-described components are mixed and packaged in a storage/applicator device suitable for oral administration of a free-flowing powder. Non-limiting examples of such a storage/applicator device include straws (sealed on both ends), or droppers or vial (stoppered or otherwise sealed).

The following formulation and applications examples are illustrative of the inventive tooth-whitening formulations and methods of the present invention. The components and specific ingredients of the example formulations are presented as being typical, and various modifications can be derived in view of the foregoing disclosure within the scope of the invention.

| Formulation Examples | | | | |
|---|---|---|---|---|
| | Weight (mg) | | | |
| Ingredient | Example 1 | Example 2 | Example 3 | Example 4 |
| Sodium bicarbonate | 4 | 4 | 4 | 4 |
| Silica | 2 | 2 | 2 | 2 |
| PVP | 50 | 50 | 50 | 50 |
| Calcium carbonate | 120 | 120 | 120 | 120 |
| Dicalcium phosphate | — | 30 | — | 30 |
| Xylitol | 272 | 272 | 272 | 272 |
| Starch | — | — | 10 | — |

-continued

| Formulation Examples | | | | |
|---|---|---|---|---|
| | Weight (mg) | | | |
| Ingredient | Example 1 | Example 2 | Example 3 | Example 4 |
| Microcrystalline cellulose | — | — | 40 | — |
| Carboxymethylcellulose | — | — | — | 50 |
| Magnesium stearate | 2 | 2 | 2 | 2 |

APPLICATIONS EXAMPLES

Example 3—Colorimetric (L*a*b*) Measurements

Eight subjects were tested for changes in tooth color (i.e., staining) after consuming red wine as they normally would for 90 minutes.

At baseline, and after each of following time intervals, each subject was asked to smile; high-resolution images were taken with a digital SLR camera under the same lighting conditions and camera setting conditions: (i) 30 minutes after consumption; (ii) 60 minutes after consumption; (iii) 90 minutes after consumption; and (iv) immediately after consuming the glass of wine and then ingesting a tablet composition according to Example 1.

High-resolution color prints of each image were printed and the color of the upper four middle teeth—Numbers 7-10 based on the Universal Numbering System for Permanent Dentition Phase. The Universal Numbering System for Permanent Dentition Phase assigning numbers to the teeth in the permanent dentition from 1 to 32 starting with the upper right third molar and continuing over to the upper left third molar and then down to the lower left third molar and onto to the lower right third molar. Measurements were taken with a chromameter (also known in the art as a colorimeter) using the CIE 1976 (L*a*b*) system, where "L*" value is represents comparative lightness/darkness (lower L* being indicative of darker), and "a*" and "b*" chromaticity coordinates (red-green and blue-yellow, respectively). See, A. R. Robertson, "The CIE 1976 color-difference formulae," *Color Res. Appl.* Vol. 2, pp. 7-11 (1977). Each of the L*, a* and b* can be plotted in three-dimensional space to characterize a color in absolute terms. The magnitude of the difference between two colors, as perceived by the human eye, is proportional to the distance between two points defining the two colors on the three-dimensional plot. The difference between the two colors, the Euclidean distance (ΔE), is defined by the following equation: $\Delta E^*ab = [(\Delta L^*)^2 + (\Delta a^*)^2 + (\Delta b^*)2]^{1/2}$.

|    | Subject | #1 | #2 | #3 | #4 | #5 | #6 | #7 | #8 | Avg. |
|----|---------|------|------|------|------|------|------|------|------|------|
| L* | Baseline | 44 | 52.5 | 53.1 | 57.6 | 55.8 | 57.1 | 52.6 | 57.8 | 53.8 |
|    | 30 min | 43.2 | 52.7 | 55.7 | 50.6 | 53.8 | 55.1 | 52.7 | 50.1 | 51.7 |
|    | 60 min | 43.2 | 46 | 52.8 | 49.9 | 55.4 | 55.2 | 55 | 51.2 | 51.1 |
|    | 90 min | 42 | 52.1 | 53.2 | 48.5 | 54.6 | 51.3 | 56 | 51.5 | 51.2 |
|    | Post tablet | 41 | 58.3 | 53.6 | 52 | 56.6 | 58.5 | 53.4 | 56.5 | 53.7 |
| a* | Baseline | 11.95 | 10.5 | 13.1 | 7.6 | 9.5 | 11.8 | 9.1 | 3.3 | 9.6 |
|    | 30 min | 10.5 | 10.5 | 12.3 | 6.1 | 7.7 | 11.7 | 7.2 | 4.6 | 8.8 |
|    | 60 min | 10.7 | 8.6 | 10.5 | 7 | 6.6 | 10 | 9.7 | 5 | 8.5 |
|    | 90 min | 10.8 | 10.1 | 10.1 | 8.1 | 6.8 | 11.6 | 8.8 | 5.5 | 9.0 |
|    | Post tablet | 8.7 | 7.4 | 10.2 | 4.1 | 5.1 | 9.5 | 8.1 | 3.1 | 7.0 |
| b* | Baseline | 18.9 | 17 | 19.2 | 19.9 | 15.1 | 15.9 | 16.7 | 9.2 | 16.5 |
|    | 30 min | 18.5 | 18.7 | 18.5 | 12.3 | 14.9 | 15.7 | 16.3 | 6.6 | 15.2 |
|    | 60 min | 17 | 17 | 20.6 | 13.5 | 11.9 | 12.3 | 13.4 | 5.6 | 13.9 |
|    | 90 min | 15.1 | 17.1 | 19.2 | 12.2 | 11.8 | 12.3 | 13.8 | 4.6 | 13.3 |
|    | Post tablet | 12.3 | 18.3 | 17.3 | 12.1 | 11.5 | 14.3 | 12.6 | 6.5 | 13.1 |

Figure 1:
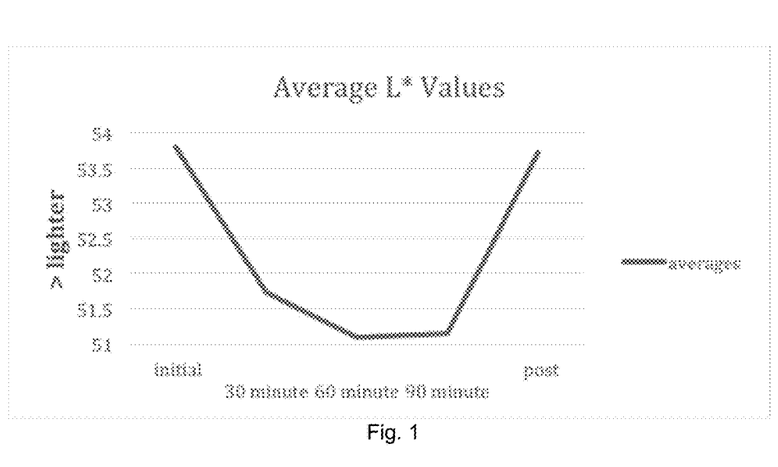
FIG. 1 shows changes in L* values when practicing the method of the present invention, namely changes in average L* after ingesting the tooth-whitening tablet of Example 1, at five time points: "initial" (i.e., before), 30 minutes, 60 minutes, 90 minutes and "post" (i.e., after) treatment.

As summarized in the above table, and represented graphically in FIG. 1, after consuming wine, L* values dropped. After practicing the method of the present invention (ingesting the tooth-whitening tablet of Example 1), L* increased, returning to almost the baseline L* value.

Figure 2:
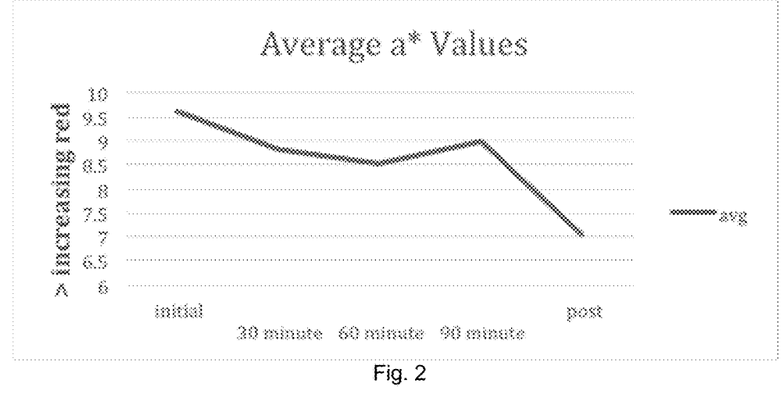
FIG. 2 shows changes in a* values when practicing the method of the present invention, namely changes in a* after ingesting the tooth-whitening tablet of Example 1, at five time points: initial, 30 minutes, 60 minutes, 90 minutes and post.

FIG. 2 shows reduction in redness (a*) of subjects' teeth after consuming a glass of red wine and thereafter ingesting a teeth-whitening tablet of Example 1.

Figure 3:
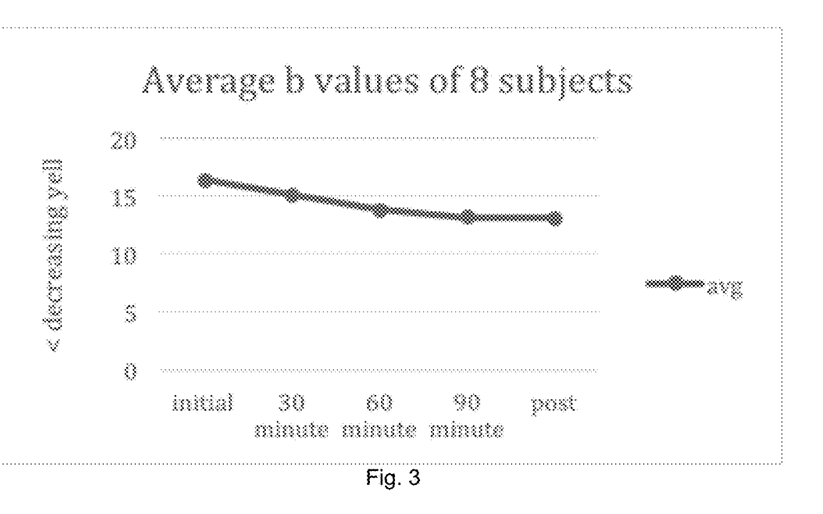
FIG. 3 shows changes in b* values when practicing the method of the present invention, namely changes in b* after ingesting the tooth-whitening tablet of Example 1, at five time points: initial, 30 minutes, 60 minutes, 90 minutes and post.
Figure 4:
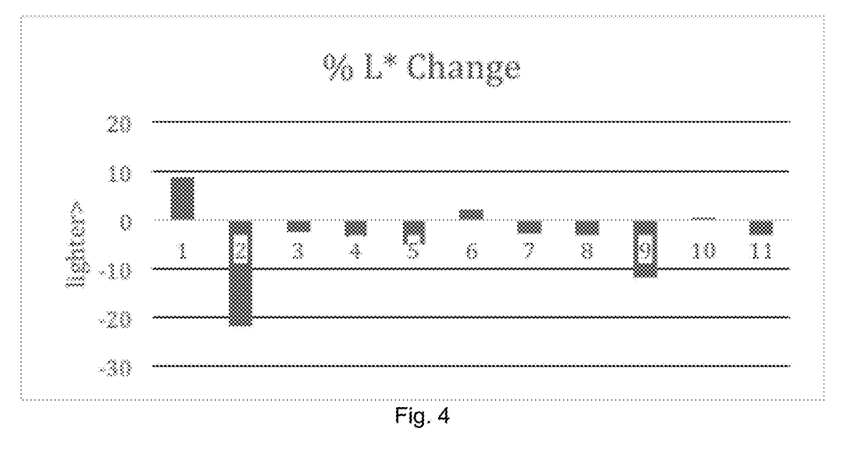
FIG. 4 shows percent change L* in eleven teeth soaked in red wine.
Figure 5:
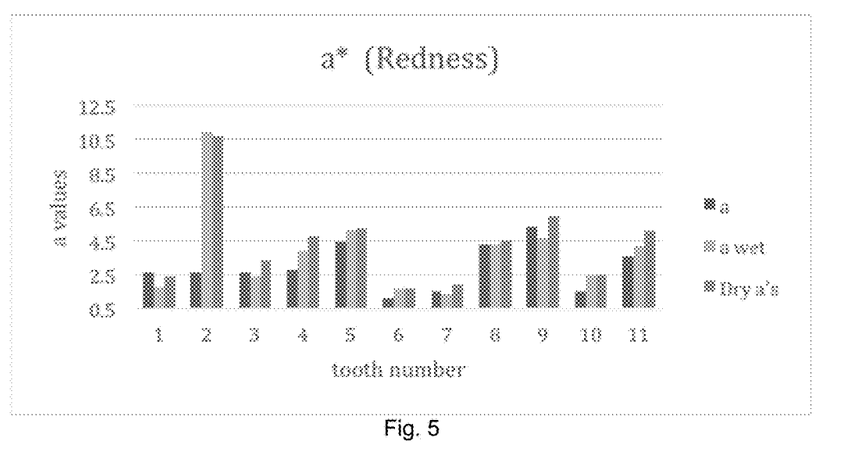
FIG. 5 shows a* (redness values) in eleven teeth soaked in red wine.
Figure 6:
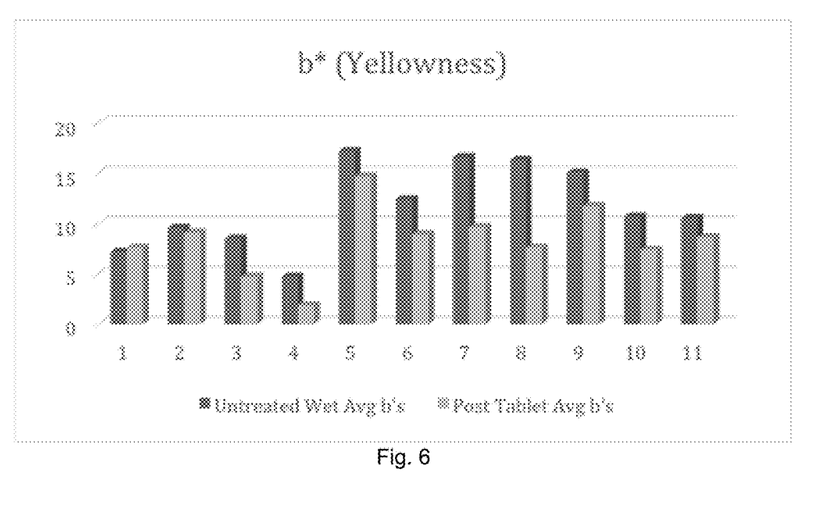
FIG. 6 shows b* yellowness values in eleven teeth soaked in red wine.
Figure 7:
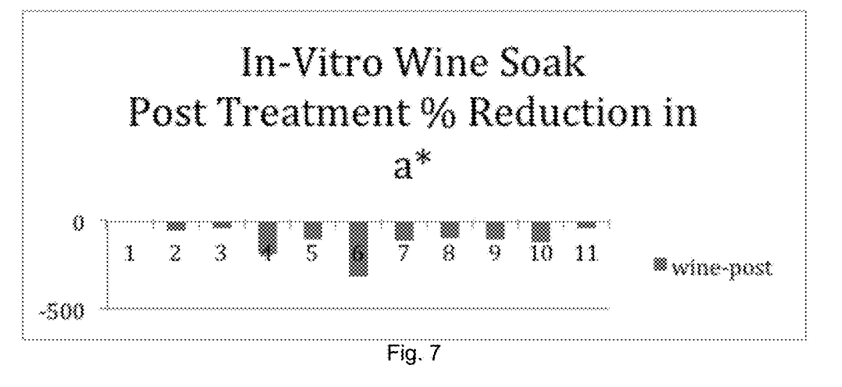
FIG. 7 shows percent reduction in a* in eleven teeth soaked in red wine.
Figure 8:
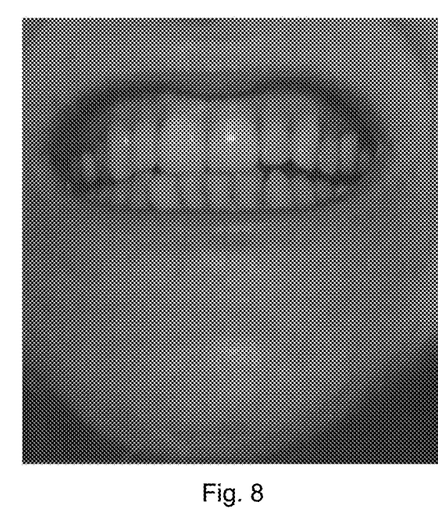
FIG. 8 shows teeth after consuming red wine.
Figure 9:
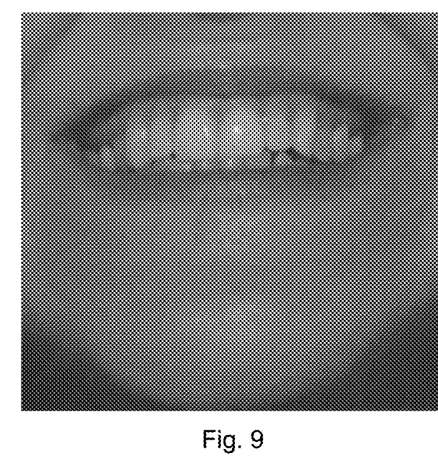
FIG. 9 shows teeth after contacting wine-stained teeth with the tablet of invention.

An increase in b* indicates tooth color is trending towards yellow; a decrease in b* means the color is trending towards blue. The average initial b* value in Example 3 was 16.5, indicative of a slightly yellow tint. The average b* value after drinking red wine decreased to 13.3, meaning average tooth color appeared less yellow. After practicing the method of the present invention (ingesting the tooth-whitening tablet of Example 1) the average b* value dropped, meaning the teeth were significantly less yellow (without becoming blue) than baseline. Changes in b* values are presented graphically in FIG. 3.

Example 4—Trained Human Visual Observation

A total of twenty images—five images (baseline, 30-minute, 60-minute, 90-minute and post-tablet) for each for subjects 5, 6, 7, and 8 from Example 3—were presented to technicians, each tested for color acuity and specifically trained to detect color differences. The technicians were each asked to rank the baseline, 90-minute and post tablet images with respect to darkness (L*) and yellow tint (b*).

19 of the 20 post-tablet images were scored as lighter (i.e., less dark) than the baseline and 90-minute images.

18 of the 20 post-tablet images were graded to be less yellow than the baseline images.

Example 5—Reduced Staining of Bovine Teeth

Bovine teeth were cleaned, dried and marked 1 through 11. The teeth were also weighed. Three baseline colorimetric measurements (L*, a*, b* values) were recorded for each tooth. Tooth #1 served as a negative control, and was placed in water alone. Tooth #2 served as a positive control, and was placed in 10 milliliters of Rex Goliath® Zinfandel Red Wine'. The remaining teeth, #s 3-11, were placed in 10 milliliters of the same Rex Goliath red wine in combination with the following additional ingredients, in amounts equivalent to Examples 1/2:

3. PVP—50 mg
4. Sodium bicarbonate—4 mg
5. Silica—2 mg; Calcium carbonate—120 mg
6. Tablet of Example 2
7. PVP—50 mg; Sodium bicarbonate—4 mg
8. PVP—50 mg; Silica—2 mg; Calcium carbonate—120 mg
9. Silica—2 mg; Calcium carbonate—120 mg; Sodium bicarbonate—4 mg
10. PVP—50 mg; Silica—2 mg; Calcium carbonate—120 mg; Sodium bicarbonate—4 mg
11. Xylitol—272 mg After soaking the teeth for 60 minutes, pH measurements were recorded. The teeth were removed from the wine, dipped in a water bath to rinse. Three colorimetric readings were then taken of each of teeth #s 3-11, as well as the two controls (#s 1 and 2). The teeth were then dried for 2 days in an oven at 45° C. Two measurements were taken on day 2, approximately one hour apart. Three colorimetric readings were again recorded. The teeth were reweighed after drying.

|    |    | Tooth # | | | | | | | | | | |
|----|----|------|------|------|------|------|------|------|------|------|------|------|
|    |    | #1 | #2 | #3 | #4 | #5 | #6 | #7 | #8 | #9 | #10 | #11 |
| L* | Baseline | 74.8 | 80.8 | 82.3 | 79.7 | 78.0 | 77.8 | 80.4 | 75.5 | 75.1 | 82.1 | 81.1 |
|    | 60 min wine bath | 77.4 | 62.2 | 73.4 | 72.3 | 74.7 | 79.5 | 75.0 | 72.2 | 69.6 | 78.4 | 70.6 |
|    | After drying at 45° C. | 81.4 | 63.3 | 80.4 | 77.0 | 74.2 | 79.4 | 78.1 | 73.1 | 66.1 | 82.2 | 74.8 |
| a* | Baseline | 2.6 | 2.6 | 2.7 | 2.8 | 4.5 | 1.1 | 1.5 | 4.3 | 5.3 | 1.5 | 3.6 |
|    | 60 min wine bath | 1.7 | 11.0 | 2.4 | 3.9 | 5.2 | 1.7 | 1.4 | 4.3 | 4.7 | 2.5 | 4.2 |
|    | After drying at 45° C. | 2.4 | 10.7 | 3.4 | 4.8 | 5.3 | 1.7 | 1.9 | 4.5 | 6.0 | 2.4 | 5.1 |

-continued

| | Tooth # | | | | | | | | | | |
|---|---|---|---|---|---|---|---|---|---|---|---|
| | #1 | #2 | #3 | #4 | #5 | #6 | #7 | #8 | #9 | #10 | #11 |
| Wt. Initial | 1.3514 | 2.3418 | 1.2208 | 1.0562 | 2.5427 | 2.5964 | 2.9365 | 1.7315 | 1.6794 | 1.9872 | 1.1732 |
| Day 2 (#1) | 1.3526 | 2.3384 | 1.2194 | 10.557 | 2.5485 | 2.6134 | 2.9524 | 1.7425 | 1.6896 | 1.9940 | 1.1840 |
| Day 2 (#1) | 1.3529 | 2.3394 | 1.2198 | 1.0564 | 2.5479 | 2.6138 | 2.9524 | 1.7422 | 1.6899 | 1.9938 | 1.1838 |
| % Change | 0.1109 | (0.1024) | (0.0819) | 0.0189 | 0.2045 | 0.6701 | 0.5414 | 0.6179 | 0.6252 | 0.3321 | 0.9035 |

L* for the wine soaked tooth alone (#2) decreased the most, indicating the highest degree of darkening. L* for tooth #6, containing all of the required ingredients of the tooth-whitening tablet of the present invention, increased - indicating lightening. a* values of all of the wine-soaked teeth (#s 2-11) increased. Notably, however, a* value for the tooth treated with the tablet of the invention (#6) increased only slightly. FIGS. 4-7 depict the changes.

| Bovine Teeth Weights | | | | |
|---|---|---|---|---|
| | Initial Dried | After Wine & Dried 2 Days HVAC 7:30 am | After Wine & Dried 2 Days HVAC 8:45 am | % Change |
| 1 | 1.3514 | 1.3526 | 1.3529 | 0.110996 |
| 2 | 2.3418 | 2.3384 | 2.3394 | −0.10249 |
| 3 | 1.2208 | 1.2194 | 1.2198 | −0.08191 |
| 4 | 1.0562 | 10.557 | 1.0564 | 0.018936 |
| 5 | 2.5427 | 2.5485 | 2.5479 | 0.204507 |
| 6 | 2.5964 | 2.6134 | 2.6138 | 0.670159 |
| 7 | 2.9365 | 2.9524 | 2.9524 | 0.541461 |
| 8 | 1.7315 | 1.7425 | 1.7422 | 0.617961 |
| 9 | 1.6794 | 1.6896 | 1.6899 | 0.625223 |
| 10 | 1.9872 | 1.994 | 1.9938 | 0.332126 |
| 11 | 1.1732 | 1.184 | 1.1838 | 0.903512 |

Tooth #2, soaked in red wine only, exhibited weight loss, indicating demineralization caused by the low pH. Tooth #3 also showed some weight loss. All of the other samples, especially teeth treated with according to the methods of the invention, showed weight gain, indicating neutralized pH mineralization to prevent tooth erosion.

| (pH) | | |
|---|---|---|
| | pH | pH Change from Wine |
| Wine Control | 3.85 | .36 |
| PVP | 3.79 | .3 |
| Sodium bicarbonate(NaHCO₃) | 3.99 | .5 |
| Silica & Calcium Carbonate(CaCO₃) | 5.29 | 1.8 |
| Invention Example 1 | 5.75 | 2.26 |
| PVP and NaHCO₃ | 4.19 | .7 |
| PVP, Silica, and CaCO₃ | 5.39 | 1.9 |
| Silica, CaCO₃, & NaHCO₃ | 5.54 | 2.05 |
| PVP, Silica, CaCO₃, & NaHCO₃ | 5.69 | 2.2 |
| Xylitol | 3.76 | .27 |

The initial pH was 3.49. pH increase of the wine control indicates that the tooth was being de-mineralized. This is confirmed in the previous example where the tooth soaked in wine only lost weight. pH increases in teeth treated in methods of the present invention. The above example, ten (10) grams of wine was used When wine is consumed in a social setting under "normal"/intended use conditions, it is unlikely that the oral cavity would have even 10% of this amount of residual wine after swallowing. Under these "normal" conditions, the pH change from practicing the methods of the present invention (i.e., with a tablet dosage form as illustrated in the examples) would be expected to become more basic.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A method of improving the cosmetic appearance of human teeth comprising:
   contacting the teeth with a whitening powder composition after ingesting a chromogenic, tannin-containing food or beverage; and
   allowing the whitening power to dissolve thereby reducing staining of the teeth caused by tannins and/or chromogens, the whitening powder composition is comprised of
   (i) at least one abrasive powder, the at least one abrasive powder being a silica compound;
   (ii) at least one buffering powder; and
   (iii) a complexing agent, the complexing agent binding to and removing the chromogenic, tannin-containing food or beverage from the teeth.

2. The method of claim 1 wherein the whitening powder composition contains at least two carbonate compounds selected from the group consisting of sodium bicarbonate and calcium carbonate.

3. The method of claim 1 wherein the whitening powder composition is comprised of sodium bicarbonate, calcium carbonate and dicalcium phosphate.

4. The method of claim 1 wherein the complexing agent is PVP.

5. The method of claim 1 wherein the whitening powder composition includes an anti-cavity sweetener, the anti-cavity sweetener being xylitol.

6. The method of claim 1 wherein the chromogenic, tannin-containing food or beverage is a red wine.

7. The method of claim 1 wherein the whitening powder composition contains at least 1 mg of sodium bicarbonate.

8. The method of claim 1 wherein the whitening powder composition contains from about 3 mg to about 15 mg of sodium bicarbonate.

9. The method of claim 1 wherein the whitening powder composition contains at least 10 mg of calcium carbonate.

10. The method of claim 9 wherein the whitening powder composition contains at least 50 mg of calcium carbonate.

11. The method of claim 1 wherein the whitening powder composition contains at least 10 mg of dicalcium phosphate.

12. The method of claim 11 wherein the whitening powder contains from about 30 to about 60 mg of dicalcium phosphate.

13. The method of claim 1 wherein the whitening powder composition contains at least 0.5 mg of the silica compound.

14. The method of claim 1 wherein the whitening powder composition contains at least 2 mg of the silica compound.

15. The method of claim 1 wherein the whitening powder composition contains at least 10 mg of PVP.

16. The method of any of claim 13 wherein the whitening powder contains from about 50 to about 100 mg of PVP.

17. The method of claim 1 where the method is practiced by passively contacting the teeth with whitening powder composition of claim 1.

18. The method of claim 1 where the composition does not contain an essential oil or flavorant.

19. A method of reducing the appearance of a stain on human teeth comprising:
   providing a tooth-whitening composition including:
      at least one abrasive powder;
      at least one buffering powder; and
      a linear polyvinyl polypyrrolidone; and
   instructing a user to ingest the tooth-whitening composition after ingesting a chromogenic, tannin-containing beverage, the tooth-whitening composition being configured to dissolve after binding to and removing the chromogenic, tannin-containing beverage from the human teeth.

20. The method of claim 19 wherein the at least one abrasive powder is at least one milligram of a silica compound.

* * * * *